(12) United States Patent
Rockrohr et al.

(10) Patent No.: US 12,137,998 B2
(45) Date of Patent: Nov. 12, 2024

(54) BINDING AND NON-BINDING ARTICULATION LIMITS FOR ROBOTIC SURGICAL SYSTEMS

(71) Applicant: Covidien LP, Mansfield, MA (US)

(72) Inventors: Brian Rockrohr, Guilford, CT (US); Eric Taylor, Southington, CT (US); Matthew Hartzsch, Glastonbury, CT (US); Colin Murphy, Cambridge, MA (US)

(73) Assignee: Covidien LP, Mansfield, MA (US)

( * ) Notice: Subject to any disclaimer, the term of this patent is extended or adjusted under 35 U.S.C. 154(b) by 783 days.

(21) Appl. No.: 17/288,961

(22) PCT Filed: Oct. 29, 2019

(86) PCT No.: PCT/US2019/058480
§ 371 (c)(1),
(2) Date: Apr. 27, 2021

(87) PCT Pub. No.: WO2020/092312
PCT Pub. Date: May 7, 2020

(65) Prior Publication Data
US 2021/0401515 A1 Dec. 30, 2021

Related U.S. Application Data

(60) Provisional application No. 62/752,456, filed on Oct. 30, 2018.

(51) Int. Cl.
*A61B 34/35* (2016.01)
*B25J 9/16* (2006.01)

(52) U.S. Cl.
CPC ............. *A61B 34/35* (2016.02); *B25J 9/1676* (2013.01)

(58) Field of Classification Search
CPC ... A61B 34/35; A61B 90/03; A61B 2090/061; A61B 2090/067; A61B 34/37;
(Continued)

(56) References Cited

U.S. PATENT DOCUMENTS

| | | | |
|---|---|---|---|
| 6,786,896 B1 * | 9/2004 | Madhani | A61B 34/30 606/1 |
| 7,741,802 B2 * | 6/2010 | Prisco | B25J 9/1689 318/632 |

(Continued)

FOREIGN PATENT DOCUMENTS

| | | |
|---|---|---|
| CN | 105101887 A | 11/2015 |
| JP | 2004135915 A | 5/2004 |

(Continued)

OTHER PUBLICATIONS

Canadian Office Action dated May 23, 2023, issued in corresponding Canadian Appln. No. 3,111,088, 4 pages.

(Continued)

*Primary Examiner* — Jaime Figueroa
(74) *Attorney, Agent, or Firm* — Carter, DeLuca & Farrell LLP

(57) ABSTRACT

A robotic surgical system and method of selectively binding articulation limits to a surgical instrument includes detecting a proximal or a distal linear movement of the surgical instrument, calculating a distance between a tool center point of the surgical instrument after the proximal or the distal linear movement and a remote center of motion, assigning and binding an articulation limit to the surgical instrument based on the calculated distance when the detected linear movement is distal linear movement, and assigning a non-binding articulation limit to the surgical instrument based on the calculated distance when the detected linear movement is proximal a linear movement.

19 Claims, 6 Drawing Sheets

(58) Field of Classification Search
CPC ............ A61B 2017/2927; B25J 9/1676; B25J 9/1689; G05B 2219/45119
USPC ................. 700/245–264; 318/568.11–568.25
See application file for complete search history.

(56) References Cited

U.S. PATENT DOCUMENTS

| | | | | |
|---|---|---|---|---|
| 7,996,110 | B2* | 8/2011 | Lipow | A61B 34/76 |
| | | | | 318/568.11 |
| 8,004,229 | B2* | 8/2011 | Nowlin | A61B 90/37 |
| | | | | 318/568.2 |
| 8,287,522 | B2* | 10/2012 | Moses | A61B 34/20 |
| | | | | 606/1 |
| 8,992,542 | B2* | 3/2015 | Hagag | A61F 2/36 |
| | | | | 606/130 |
| 9,332,987 | B2* | 5/2016 | Leimbach | A61B 18/1445 |
| 9,532,838 | B2* | 1/2017 | Coste-Maniere | A61B 34/35 |
| 9,566,122 | B2* | 2/2017 | Bowling | A61B 34/20 |
| 9,775,681 | B2* | 10/2017 | Quaid | A61N 1/372 |
| 9,820,818 | B2* | 11/2017 | Malackowski | A61B 34/20 |
| 9,943,964 | B2* | 4/2018 | Hares | A61B 34/32 |
| 10,034,718 | B2* | 7/2018 | Griffiths | B25J 9/1669 |
| 10,136,949 | B2* | 11/2018 | Felder | A61B 34/30 |
| 10,299,868 | B2* | 5/2019 | Tsuboi | B25J 9/1674 |
| 10,314,661 | B2* | 6/2019 | Bowling | A61B 34/37 |
| 10,441,372 | B2* | 10/2019 | Devengenzo | H01R 13/6582 |
| 10,464,209 | B2* | 11/2019 | Ho | A61B 34/37 |
| 2001/0018591 | A1 | 8/2001 | Brock et al. | |
| 2008/0221731 | A1 | 9/2008 | Wang et al. | |
| 2010/0041945 | A1 | 2/2010 | Isbell, Jr. | |
| 2011/0125165 | A1 | 5/2011 | Simaan et al. | |
| 2014/0246471 | A1 | 9/2014 | Jaworek et al. | |
| 2014/0249557 | A1* | 9/2014 | Koch, Jr. | A61B 17/07207 |
| | | | | 606/170 |
| 2015/0133960 | A1* | 5/2015 | Lohmeier | A61B 90/40 |
| | | | | 606/130 |
| 2015/0238276 | A1 | 8/2015 | Atarot et al. | |
| 2016/0331482 | A1* | 11/2016 | Hares | A61B 34/35 |
| 2017/0367774 | A1 | 12/2017 | Scholan | |
| 2018/0250084 | A1 | 9/2018 | Kopp et al. | |
| 2019/0022857 | A1* | 1/2019 | Conus | B25J 9/0006 |
| 2019/0038283 | A1* | 2/2019 | Shelton, IV | A61B 34/30 |
| 2019/0069962 | A1* | 3/2019 | Tabandeh | A61B 34/25 |
| 2019/0328475 | A1* | 10/2019 | Arai | A61B 34/30 |
| 2020/0054401 | A1* | 2/2020 | Yu | B25J 9/1633 |
| 2020/0253678 | A1* | 8/2020 | Hulford | A61B 34/25 |

FOREIGN PATENT DOCUMENTS

| | | |
|---|---|---|
| JP | 2016512990 A | 5/2016 |
| JP | 2016520345 A | 7/2016 |
| JP | 2017538587 A | 12/2017 |
| KR | 20150051315 A | 5/2015 |
| WO | 2017181153 A1 | 10/2017 |
| WO | 2018109851 A1 | 6/2018 |

OTHER PUBLICATIONS

International Search Report and Written Opinion of the International Searching Authority issued in corresponding application PCT/US2019/058480 mailed Feb. 12, 2020 (12 pages).

Extended European Search Report issued in corresponding application EP 19880147.4 dated Aug. 18, 2022 (9 pages).

Office Action issued in corresponding Japanese Application No. 2021-515481 mailed May 16, 2022, together with English language translation (6 pages).

Office Action issued in corresponding Japanese Application No. 2021-087355 mailed May 16, 2022, together with English language translation (5 pages).

Office Action issued in Chinese Patent Application No. 2019800607941 dated Feb. 19, 2024 (14 pages).

* cited by examiner

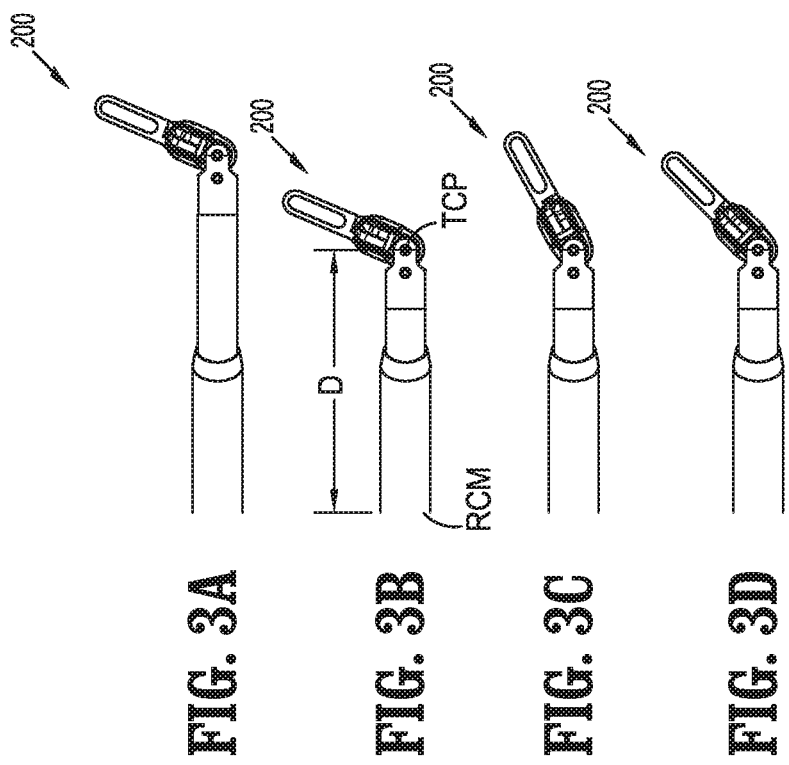
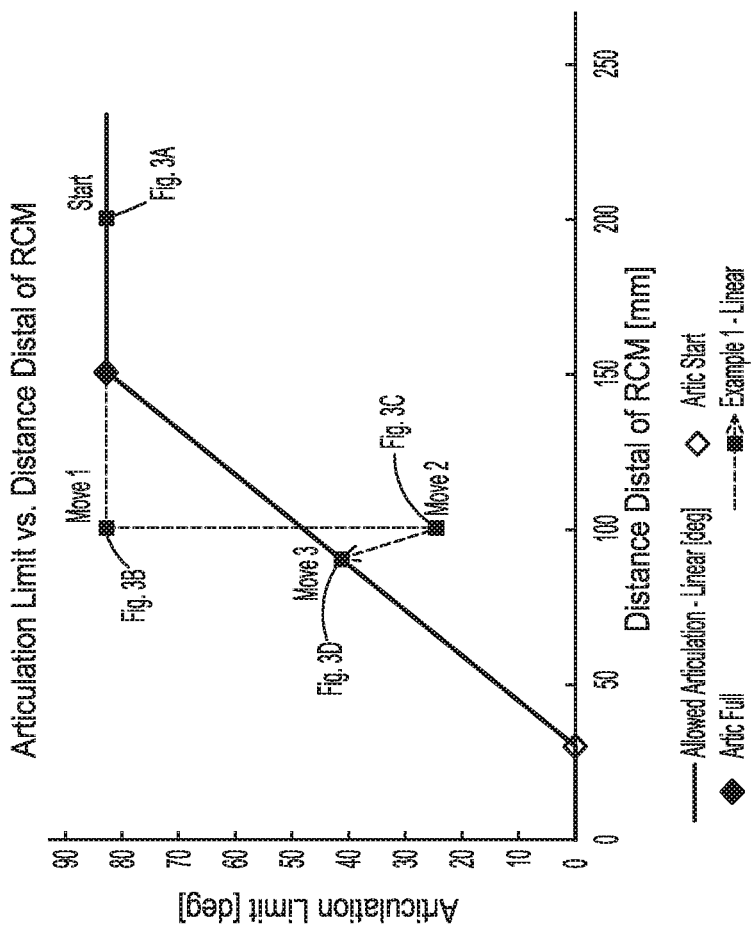

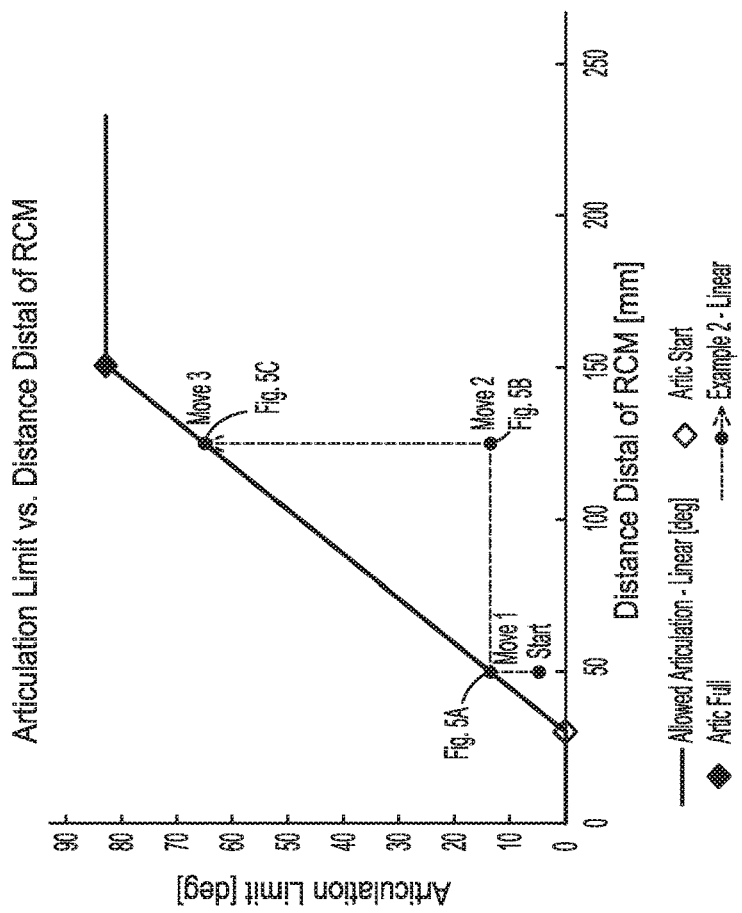
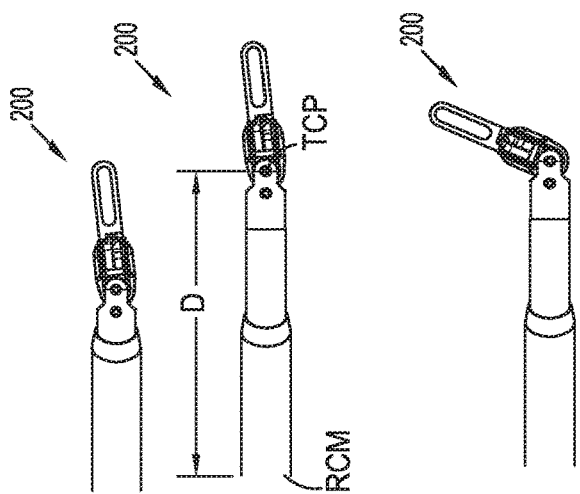

BINDING AND NON-BINDING ARTICULATION LIMITS FOR ROBOTIC SURGICAL SYSTEMS

CROSS-REFERENCE TO RELATED APPLICATIONS

This application is a U.S. National Stage Application filed under 35 U.S.C. § 371(a) of International Patent Application No. PCT/US2019/058480, filed Oct. 29, 2019, which claims the benefit of the filing date of provisional U.S. Patent Application No. 62/752,456 filed Oct. 30, 2018.

BACKGROUND

Robotic surgical systems have been used in minimally invasive medical procedures in which surgical instruments were inserted through surgical portals or access ports at fixed entry points into the patient's body. These systems incorporated a Remote Center of Motion (RCM) to ensure that the surgical instruments did not move beyond these fixed entry points as the instruments were manipulated inside the patient's body. Many of these surgical robots used a mechanical RCM with a portion of robotic arm attaching directly to the surgical portal. Unlike surgical robots using mechanical RCM's, software-based RCM's typically did not mechanically connect to the surgical portal in order to provide an increased range of motion and reduce collisions between robotic arms of the surgical robot.

As an operator of a robotic surgical system manipulates a surgical instrument within a surgical site, abrupt changes in joint constraints may occur due limitations in the surgical site, the amount in which the surgical instrument protrudes from an access port, and the distance of the distal portion of the surgical instrument from the RCM.

Accordingly, there is a need for robotic surgical systems with software-based and mechanical-based RCM's that facilitate instrument articulation control limitations in real time during a robotic surgical procedure.

SUMMARY

The present disclosure is directed to a system and method for selectively binding articulation limits to a surgical instrument.

In one aspect, a method of selectively binding articulation limits to a surgical instrument includes detecting a proximal or a distal linear movement of the surgical instrument, calculating a distance between a tool center point of the surgical instrument after the proximal or the distal linear movement and a remote center of motion, assigning and binding an articulation limit to the surgical instrument based on the calculated distance when the detected linear movement is distal linear movement, and assigning a non-binding articulation limit to the surgical instrument based on the calculated distance when the detected linear movement is proximal linear movement.

The method may further include determining a current articulation angle of the surgical instrument when the detected linear movement is proximal linear movement, and determining when the current articulation angle of the surgical instrument is greater than the assigned non-binding articulation limit. In an aspect, when the current articulation angle of the surgical instrument is greater than the assigned non-binding articulation limit, the current articulation angle of the surgical instrument is not impacted and the surgical instrument remains unbound by the non-binding articulation limit. Additionally, or alternatively, when the current articulation angle of the surgical instrument is not greater than the assigned non-binding articulation limit, the method further includes articulating the surgical instrument to a new articulation angle based on a received user command, and determining when the new articulation angle of the surgical instrument is less than the assigned non-binding articulation limit. Additionally, or alternatively, when the new articulation angle is determined to not be less than the assigned non-binding articulation limit, the new articulation angle of the surgical instrument is not impacted and the surgical instrument remains unbound by the non-binding articulation limit. Additionally, or alternatively, when the new articulation angle is determined to be less than the assigned non-binding articulation limit, the new articulation angle of the surgical instrument is not impacted and the method further includes converting the non-binding articulation limit to a binding articulation limit.

The binding articulation limit and the non-binding articulation limit may be based on an articulation limit ramp including at least one of a linear, a quadratic, a power curve, or some other shape.

In another aspect of the present disclosure a robotic surgical system is provided. The robotic surgical system includes a surgical robotic arm including a surgical instrument disposed on a distal portion thereof and a controller operably coupled to the surgical robotic arm. The controller is configured to establish a software-based remote center of motion of the surgical instrument the surgical robot arm based on a location of a surgical portal in a patient through which the surgical instrument is inserted, detect a proximal or a distal linear movement of the surgical instrument, calculate a distance between a tool center point of the surgical instrument after the proximal or the distal linear movement and the remote center of motion, assign and bind an articulation limit to the surgical instrument based on the calculated distance when the detected linear movement is distal linear movement, and assign a non-binding articulation limit to the surgical instrument based on the calculated distance when the detected linear movement is proximal linear movement.

In an aspect, the controller is further configured to determine a current articulation angle of the surgical instrument when the detected linear movement is proximal linear movement, and determine when the current articulation angle of the surgical instrument is greater than the assigned non-binding articulation limit. In an aspect, when the current articulation angle of the surgical instrument is greater than the assigned non-binding articulation limit, the current articulation angle of the surgical instrument is not impacted and the surgical instrument remains unbound by the non-binding articulation limit.

Additionally, or alternatively, when the current articulation angle of the surgical instrument is not greater than the assigned non-binding articulation limit, the controller may be further configured to articulate the surgical instrument to a new articulation angle based on a received user command, and determine when the new articulation angle of the surgical instrument is less than the assigned non-binding articulation limit. Additionally, or alternatively, when the new articulation angle is determined to not be less than the assigned non-binding articulation limit, the new articulation angle of the surgical instrument is not impacted and the surgical instrument remains unbound by the non-binding articulation limit. Additionally, or alternatively, when the new articulation angle is determined to be less than the assigned non-binding articulation limit, the new articulation angle of the surgical instrument is not impacted and the controller converts the non-binding articulation limit to a binding articulation limit.

The binding articulation limit and the non-binding articulation limit may be based on an articulation limit ramp including at least one of a linear, a quadratic, a power curve, or some other shape.

In yet another aspect of the present disclosure, a non-transitory computer-readable storage medium is provided. The computer-readable storage medium is encoded with a program that when executed by a processor performs a method including detecting a proximal or a distal linear movement of a surgical instrument, calculating a distance between a tool center point of the surgical instrument after the proximal or the distal linear movement and a remote center of motion, assigning and binding an articulation limit to the surgical instrument based on the calculated distance when the detected linear movement is distal linear movement, and assigning a non-binding articulation limit to the surgical instrument based on the calculated distance when the detected linear movement is proximal linear movement.

The method may further include determining a current articulation angle of the surgical instrument when the detected linear movement is proximal linear movement, and determining when the current articulation angle of the surgical instrument is greater than the assigned non-binding articulation limit. In an aspect, when the current articulation angle of the surgical instrument is greater than the assigned non-binding articulation limit, the current articulation angle of the surgical instrument is not impacted and the surgical instrument remains unbound by the non-binding articulation limit. Additionally, or alternatively, when the current articulation angle of the surgical instrument is not greater than the assigned non-binding articulation limit, the method further includes articulating the surgical instrument to a new articulation angle based on a received user command, and determining when the new articulation angle of the surgical instrument is less than the assigned non-binding articulation limit. Additionally, or alternatively, when the new articulation angle is determined to not be less than the assigned non-binding articulation limit, the new articulation angle of the surgical instrument is not impacted and the surgical instrument remains unbound by the non-binding articulation limit. Additionally, or alternatively, when the new articulation angle is determined to be less than the assigned non-binding articulation limit, the new articulation angle of the surgical instrument is not impacted and the method further includes converting the non-binding articulation limit to a binding articulation limit.

The binding articulation limit and the non-binding articulation limit may be based on an articulation limit ramp including at least one of a linear, a quadratic, a power curve, or some other shape.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 3A-3D are views of a distal portion of a surgical instrument during proximal linear retraction of the surgical instrument while the surgical instrument is being controlled in accordance with the method of FIG. 2;

FIG. 4 is a graph showing articulation limits vs. distance of the surgical instrument, distal of the RCM, during proximal linear retraction of the surgical instrument;

FIGS. 5A-5C are views of a distal portion of a surgical instrument during distal linear advancement of the surgical instrument while the surgical instrument is being controlled in accordance with the method of FIG. 2;

FIG. 6 is a graph showing articulation limits vs. distance of the surgical instrument, distal of the RCM, during distal linear advancement of the surgical instrument;

DETAILED DESCRIPTION

Figure 1:
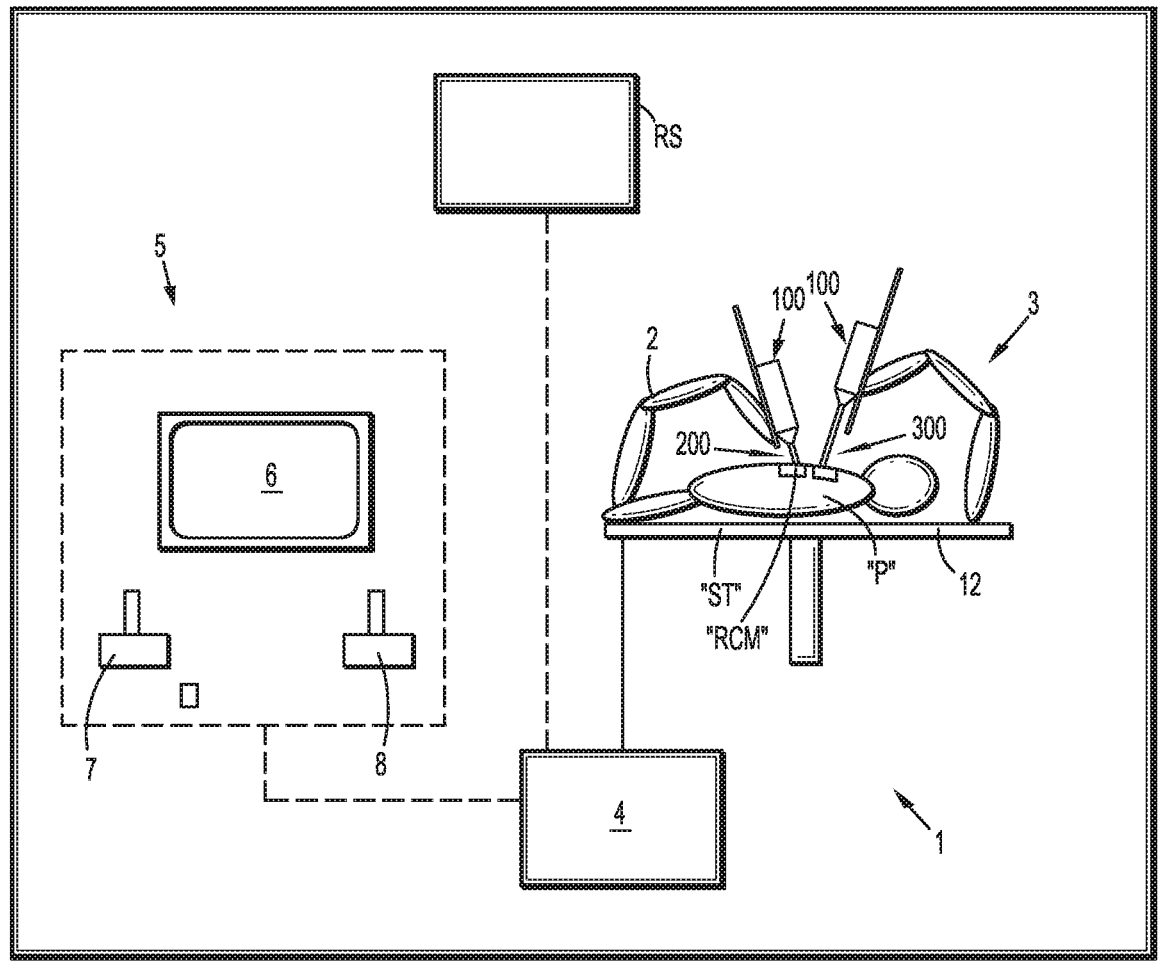
FIG. 1 is a schematic illustration of a robotic surgical system in accordance with the present disclosure.
Figure 2:
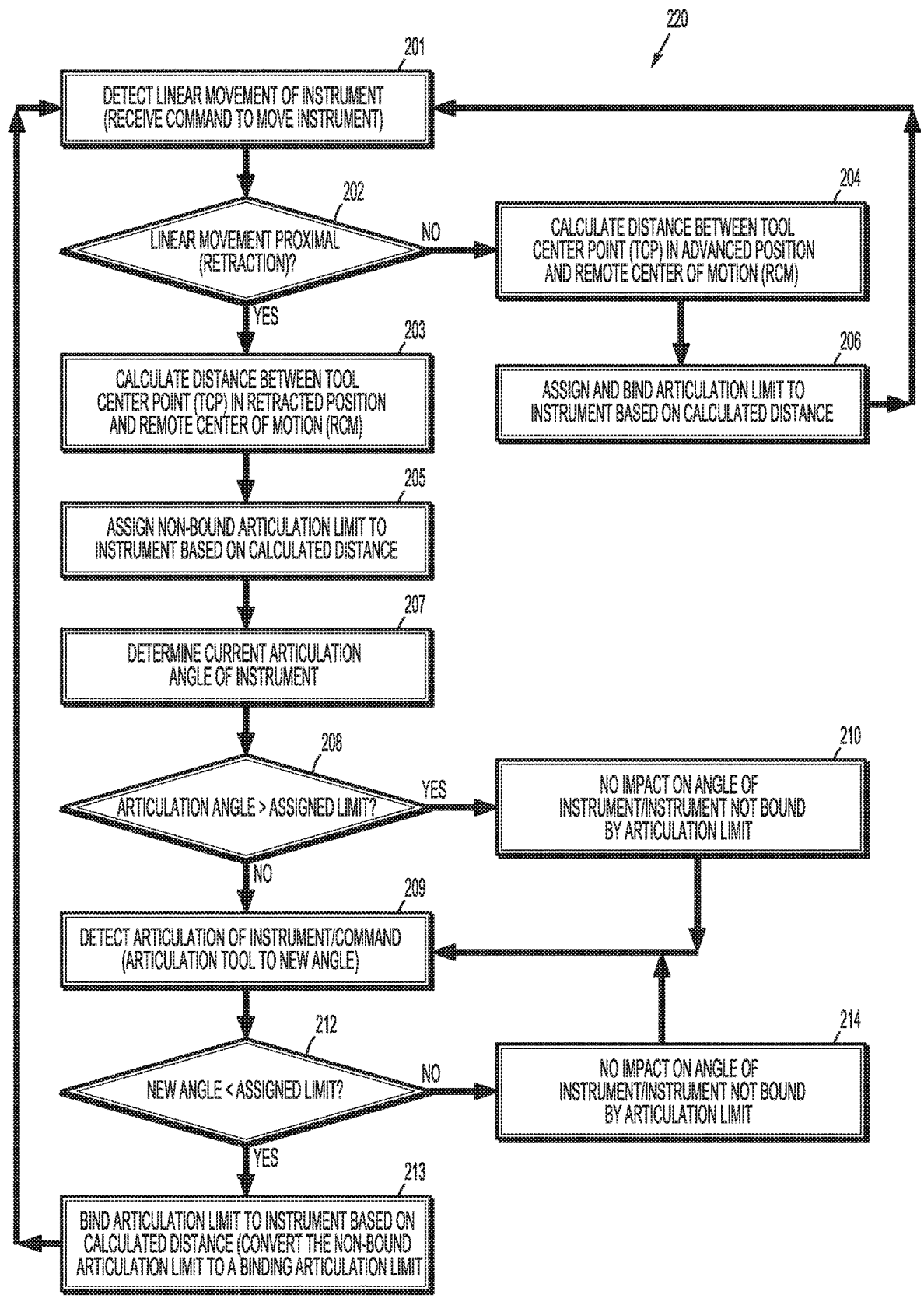
FIG. 2 is a flow chart illustrating a method of selectively binding articulation limits to a surgical instrument in accordance with an aspect of the present disclosure.
Figure 7:
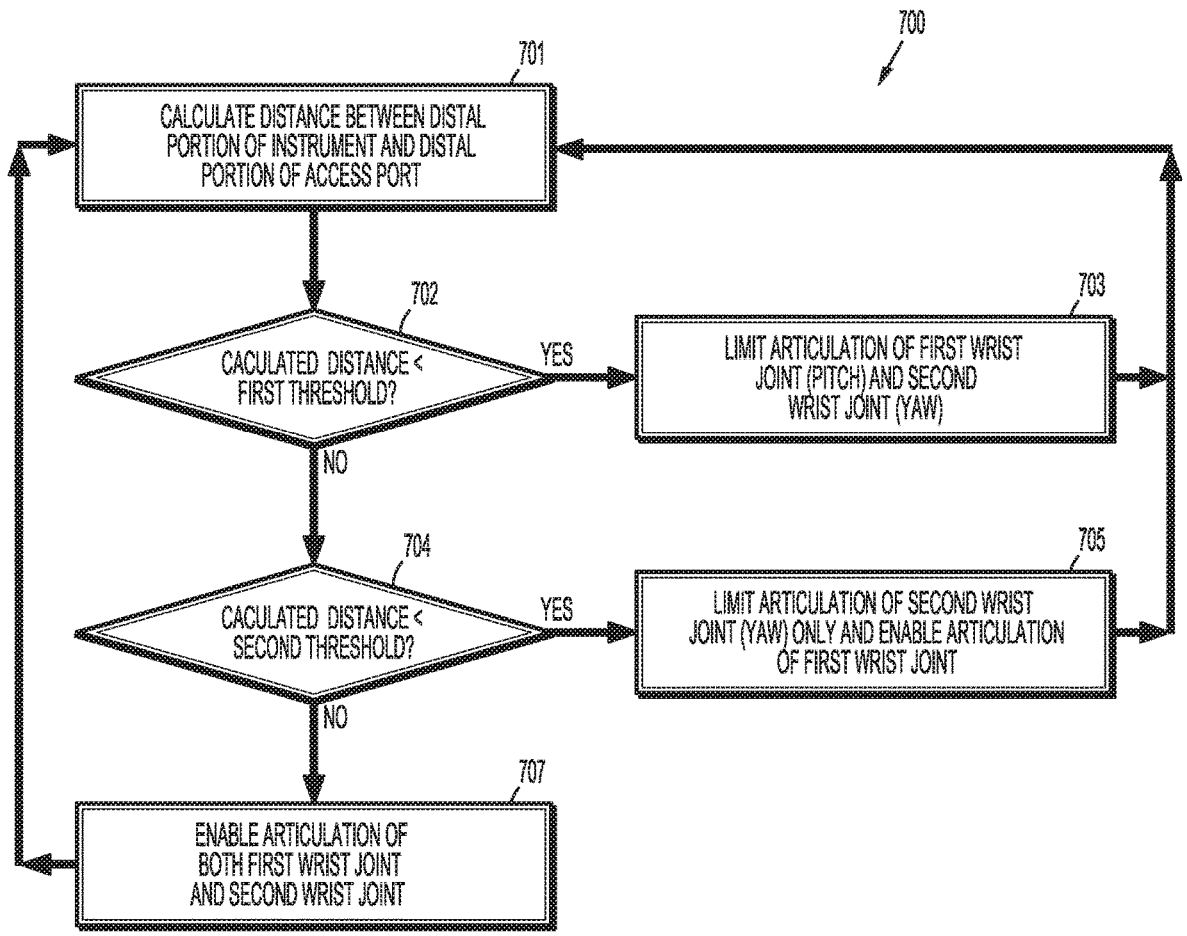
FIG. 7 is a method for selectively limiting articulation of selective joints of a surgical instrument in accordance with an aspect of the present disclosure.

Embodiments of the present disclosure are described in detail with reference to the drawings, in which like reference numerals designate identical or corresponding elements in each of the several views. As used herein, the term "distal" refers to that portion of a device that is farther from the user or robotic component, while the term "proximal" refers to that portion of a device that is closer to the user or robotic component.

Referring initially to FIG. 1, a surgical system, such as, for example, a robotic surgical system is shown generally as robotic surgical system 1 and generally includes a plurality of robotic arms 2, 3; a controller or control device 4; and an operating console 5 coupled with control device 4. Operating console 5 includes a display device 6, which may be set up to display three-dimensional images; and manual input devices 7, 8, by means of which a person (not shown), for example a surgeon, is able to telemanipulate robotic arms 2, 3 in a first operating mode, as known in principle to a person skilled in the art.

Robotic surgical system 1 also includes a surgical assembly 100 connected to a distal end of each of robotic arms 2, 3. Surgical assembly 100 may support one or more surgical instruments such as surgical instrument 200 as will be described in greater detail below. Each of the robotic arms 2, 3 is composed of a plurality of members, which are connected through joints. Robotic arm 2 (and/or robotic arm 3) includes a mounting portion that functions to support surgical instrument 200.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, their surgical assemblies 100 and/or surgical instrument 200 execute a desired movement according to a movement defined by means of manual input devices 7, 8. Control device 4 may also be set up in such a way that it regulates movement of robotic arms 2, 3 and/or of the drives. While electrically coupled to controller or control device 4, as described above, robotic arms 2, 3 are configured to receive signals from control device 4, which may be software-based, to establish a remote center of motion "RCM" at any suitable location.

Robotic surgical system 1 is configured for use on a patient "P" lying on a patient table 12 to be treated in a minimally invasive manner by means of an end effector of one or more of the surgical instruments 200, 300. Surgical system 1 may also include more than two robotic arms 2, 3, the additional robotic arms likewise being connected to control device 4 and being telemanipulatable by means of operating console 5. One or more additional surgical assemblies 100 and/or surgical instrument 200 may also be attached to the additional robotic arm.

Control device 4 may control a plurality of motors with each motor configured to drive a relaxing or a pulling of one or more cables of surgical instruments 200, 300. In use, as these cables are relaxed or pulled, the one or more cables effect operation and/or movement of end effectors of surgical instruments 200, 300. It is contemplated that control device 4 coordinates the activation of the various motors to coordinate a relaxing or a pulling motion of these cables in order to coordinate an operation and/or movement (e.g., linear movement, articulation, rotation, etc.) of end effectors of surgical instruments 200, 300. Reference may be made to International Application No. PCT/US2014/61329, filed on Oct. 20, 2014, entitled "Wrist and Jaw Assemblies for Robotic Surgical Systems," the entire content of which is incorporated herein by reference, for a detailed discussion of the construction and operation of end effectors and other aspects of the robotic surgical system.

Control device 4 can include any suitable logic control circuit adapted to perform calculations and/or operate according to a set of instructions. Control device 4 can be configured to communicate with a remote system "RS," either via a wireless (e.g., Wi-Fi, Bluetooth, LTE, etc.) and/or wired connection. Remote system "RS" can include data, instructions and/or information related to the various components, algorithms, and/or operations of system 1. Remote system "RS" can include any suitable electronic service, database, platform, cloud, or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions, which may be pre-programmed and/or input by a user. Control device 4 can be configured to accept a plurality of user inputs from a user interface (e.g., switches, buttons, touch screen, etc. of operating console 5) which may be coupled to remote system "RS."

Reference may be made to U.S. Pat. No. 8,828,023, filed on Nov. 3, 2011, entitled "Medical Workstation," the entire content of which is incorporated herein by reference, for a detailed discussion of the construction and operation of components of robotic surgical system 1.

Turning now to FIGS. 2, 3A-3D, 4, 5A-5C, and 6, a method of selectively binding articulation limits to a surgical instrument 200 will now be described with particular detail and will be referred to as method 220. The steps of the methods described herein, although described in a particular order, may be implemented in any order, and may include some or all of the steps described. Additionally, the methods described herein, although described as being carried out by a control device of a robotic surgical system (e.g., remote system "RS," control device 4, etc.), may be carried out by any component of a surgical instrument or surgical robotic system.

Method 220 begins at step 201 where linear movement of a surgical instrument 200 is detected. The detection in step 201 may be made from receipt of a command to cause linear movement of the surgical instrument 200 (e.g., prior to actual movement of the surgical instrument 200) or by other detection means (e.g., image-based analysis detecting a linear movement of the surgical instrument 200 after the surgical instrument 200 has moved from one position to another). In step 202, control device 4 determines when the linear movement of the surgical instrument 200, detected in step 201, is proximal retraction of the surgical instrument 200 or distal advancement of the surgical instrument 200. Some or all of the steps of method 220 that are described as being carried out when control device 4 determines when the linear movement of the surgical instrument 200 is proximal retraction (YES, in step 202), may additionally or alternatively be carried out when control device 4 determines when the linear movement of the surgical instrument 200 is not proximal retraction (NO, in step 202). Further, some or all of the steps of method 220 that are described as being carried out when control device 4 determines when the linear movement of the surgical instrument 200 is not proximal retraction (NO, in step 202), may additionally or alternatively be carried out when control device 4 determines when the linear movement of the surgical instrument 200 is proximal retraction (YES, in step 202).

When control device 4 determines that the linear movement is proximal retraction of the surgical instrument 200 (YES, in step 202), as opposed to distal advancement, then method 220 proceeds to step 203 where control device 4 calculates a distance between the tool center point "TCP" and a remote center of motion "RCM" after the proximal retraction is complete. FIG. 3A illustrates a position of the surgical instrument 200 prior to the proximal retraction and FIG. 3B illustrates a position of the surgical instrument 200 subsequent the proximal retraction, with the distance between the tool center point "TCP" and the remote center of motion "RCM" shown as distance "D." Such a distance may be calculated by image analysis or, in an aspect, the positions of the tool center point "TCP" and the remote center of motion "RCM" may be known and tracked by control device 4 and the distance may be calculated as the difference between the two known positions.

After the distance between the tool center point "TCP" and the remote center of motion "RCM" is calculated in step 203, method 220 proceeds to step 205 where control device 4 assigns a non-binding articulation limit to the surgical instrument 200 based on the calculated distance between the tool center point "TCP" and the remote center of motion "RCM".

In step 207, control device 4 determines the current articulation angle of the surgical instrument 200 with the surgical instrument 200 in the proximally retracted position (FIG. 3B). Such a determination may be made via image analysis or, in an aspect, the articulation angle of the surgical instrument 200 may be known and tracked by control device 4. In step 208, control device 4 determines when the articulation angle determined in step 207 is greater than an assigned limit. In an aspect, the assigned limit is equal to the non-binding articulation limit assigned in step 205 (or the binding articulation limit assigned in step 206).

When the control device 4 determines that the current articulation angle of the surgical instrument 200 (in the proximally retracted position illustrated in FIG. 3B) is greater than the assigned limit (YES, in step 208), then method 220 proceeds to step 210 where control device 4 performs no action on the articulation angle of the surgical instrument 200. In particular, in step 210, when the current articulation angle of the surgical instrument 200 is greater than the assigned non-binding articulation limit, the current articulation angle of the surgical instrument 200 is not impacted and the surgical instrument 200 remains unbound by the non-binding articulation limit.

Alternatively, when the control device 4 determines that the current articulation angle of the surgical instrument 200 (in the proximally retracted position illustrated in FIG. 3B) is not greater than the assigned limit (NO, in step 208), then method 220 proceeds to step 209 where control device 4 articulates the surgical instrument 200 to a new articulation angle (based on a received command to articulate the surgical instrument 200) and in step 212, determines when the new articulation angle of the surgical instrument 200 is less than the assigned non-binding articulation limit. FIGS. 3C and 3D illustrate the surgical instrument 200 after being articulated to respective new articulation angles from its initial articulation angle represented in FIG. 3B.

When the control device 4 determines that the new articulation angle of the surgical instrument 200 (shown in FIG. 3C) is not less than the assigned non-binding articulation limit (NO, in step 212), then method 220 proceeds to step 214 where the control device 4 keeps the surgical instrument 200 assigned to a non-binding articulation limit. In particular, in step 214, there is no impact on the articulation angle of the surgical instrument 200 and the surgical instrument 200 remains unbound by an articulation limit. Thus, in this scenario, because the assigned limit is unbound, the surgical instrument 200 may still articulate beyond the assigned limit (e.g., may articulate to a lower angular value) when the operator or control device 4 so desires.

Alternatively, when the control device 4 determines that the new articulation angle of the surgical instrument 200 (shown in FIG. 3D) is less than the assigned non-binding articulation limit (YES, in step 212), then method 220 proceeds to step 213 where the control device 4 converts the non-binding articulation limit to a binding articulation limit. In particular, in step 213 the articulation angle of the surgical instrument 200 is not impacted, but the surgical instrument 200 is now bound by an articulation limit, because of the surgical instrument 200 has now articulated beyond a non-binding articulation limit (e.g., to an angular value less than the non-binding limit angular value).

Thus, with this configuration according to method 220, the surgical instrument 200 is capable of articulating beyond an articulation limit (at certain distances from the remote center point) and only becomes bound to an articulation limit after the surgical instrument 200 has already been articulated beyond (e.g., to a lower angular value) the non-binding articulation limit assigned. FIG. 4 is a chart of exemplary binding (and non-binding) articulation limits assigned to a surgical instrument 200 during the movements (e.g., proximal retractions and articulations) of the surgical instrument 200 illustrated throughout FIGS. 3A-3D.

Turning back to step 201 of method 220, when control device 4 determines that the linear movement is distal advancement (as opposed to proximal retraction) of the surgical instrument 200 (YES, in step 202), then method 220 proceeds to step 204 where control device 4 calculates a distance between the tool center point "TCP" and a remote center of motion "RCM" after the distal advancement is complete. FIG. 5A illustrates a position of the surgical instrument 200 prior to distal advancement and FIG. 5B illustrates a position of the surgical instrument 200 subsequent the distal advancement, with the distance between the tool center point "TCP" and the remote center of motion "RCM" shown as distance "D." Such a distance may be calculated by image analysis or, in an aspect, the positions of the tool center point "TCP" and the remote center of motion "RCM" may be known and tracked by control device 4 and the distance may be calculated as the difference between the two known positions.

After the distance between the tool center point "TCP" and the remote center of motion "RCM" is calculated in step 204, method 220 proceeds to step 206 where control device 4 assigns and binds an articulation limit to the surgical instrument 200 based on the calculated distance between the tool center point "TCP" and the remote center of motion "RCM" in its distally advanced position (FIG. 5B). Should the control device 4 then receive a command to articulate the surgical instrument 200 to a new angle, the articulation angle will be limited to the assigned binding limit and will be prevented from articulating past the bound limit angle. FIG. 5C illustrates the surgical instrument 200 articulated to a new articulation angle and being limited by the bound articulation limit.

FIG. 6 is a chart of exemplary binding articulation limits assigned to a surgical instrument 200 during the movements (e.g., distal advancements and articulations) of the surgical instrument 200 illustrated throughout FIGS. 5A-5C.

Subsequent to step 206, method 220 reverts back to step 201. Thus, upon detection of further distal advancement of the surgical instrument 200, control device 4 calculates a new distance between the tool center point "TCP" and the remote center of motion "RCM" (repeats step 204) and thus, assigns a new (e.g., higher) binding articulation limit for the surgical instrument 200 based on the new calculated distance. Subsequent to step 206, in certain instances, method 220 also reverts back to step 207, which is described above.

Turning now to FIGS. 7 and 8A-8C, a method of selectively limiting articulation of multiple wrists joints of a surgical instrument 200 will now be described with particular detail and will be referred to as method 700. The steps of the methods described herein, although described in a particular order, may be implemented in any order, and may include some or all of the steps described. Additionally, the methods described herein, although described as being carried out by a control device 4 of a robotic surgical system, may be carried out by any component of a surgical instrument or surgical robotic system.

Figure 8A:
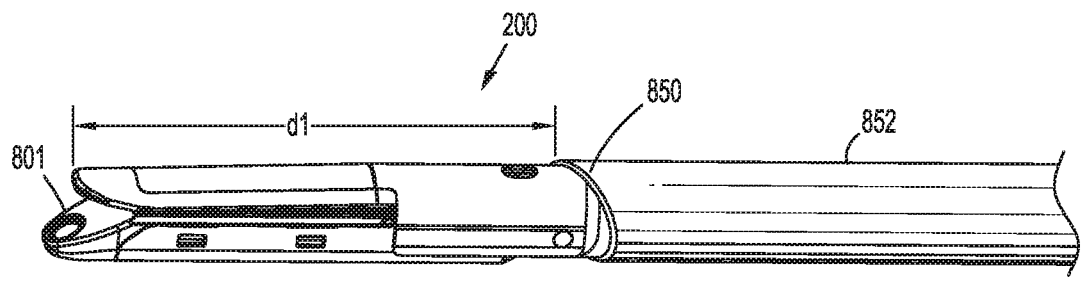
FIGS. 8A-8C are views of a distal portion of a surgical instrument at various distances from an access point and controlled by the method of FIG. 7.
Figure 8B:
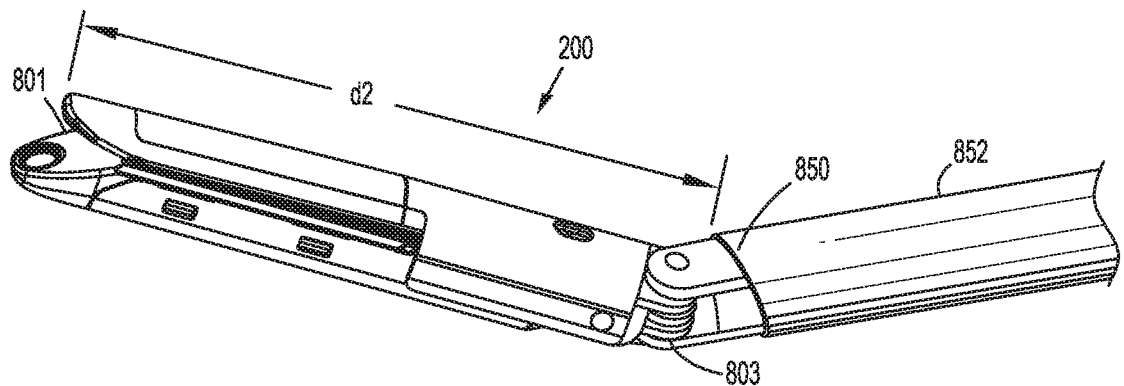
Figure 8C:
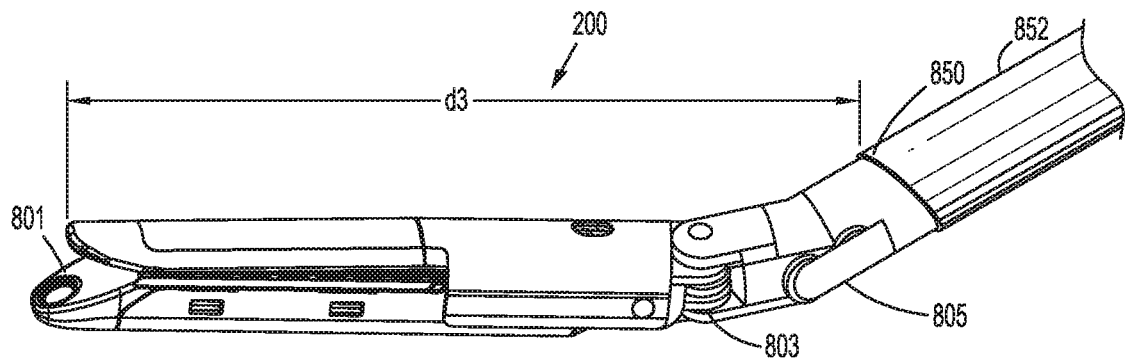

Method 700 begins at step 701 where control device 4 calculates a distance between a distal portion 801 (FIGS. 8A-8C) of a surgical instrument 200 and a distal portion 850 (FIGS. 8A-8C) of an access port 852 through which the surgical instrument 200 is positioned. Referring to FIGS. 8A-8C, a surgical instrument 200 is positioned through an access port 852, emerging from a distal portion 850 of the access port 852. Surgical instrument 200 includes a distal portion 801, a first wrist joint 803, and a second wrist joint 805. The first wrist joint 803 and the second wrist joint 805 function to enable articulation of the surgical instrument 200 about respective pivoting axes. In step 701, such a distance may be calculated by image analysis or, in an aspect, the positions of the distal portion 801 of the surgical instrument 200 the distal portion 850 of the access port 852 may be known and tracked by control device 4 and the distance may be calculated as the difference between the two known positions.

In step 702, control device 4 determines when the distance calculated in step 701 is less than a first threshold distance. When the distance is less than a first threshold distance (YES, in step 702), then method 700 proceeds to step 703 where control device 4 limits articulation of both of the first wrist joint and the second wrist joint. Alternatively, when the distance is not less than a first threshold distance (NO, in step 702), then method 700 proceeds to step 704 where control device 4 determines when the distance calculated in step 701 is less than a second threshold distance. The second threshold distance is a greater distance value than the first threshold distance.

When the distance is less than the second threshold distance (YES, in step 704), then method 700 proceeds to step 705 where control device 4 limits articulation of only the second wrist joint and enables articulation of the first wrist joint. Alternatively, when the distance is not less than the second threshold distance (NO, in step 704), then method 700 proceeds to step 707 where control device 4 enables full articulation of both of the first wrist joint and the second wrist joint.

FIG. 8A illustrates a surgical instrument 200 when a distance "d1" between the distal portion 801 of the surgical instrument 200 and a distal portion 850 of the access port 852 through which it is positioned is less than a first threshold distance. In this scenario, both the first wrist joint (not shown) and the second wrist joint (not shown) are assigned articulation limits. For example, in this scenario, first and second wrist joints (not shown) are prevented from any articulation by control device 4.

FIG. 8B illustrates a surgical instrument 200 when a distance "d2" between the distal portion 801 of the surgical instrument 200 and a distal portion 850 of the access port 852 through which it is positioned is greater than a first threshold distance but less than a second threshold distance. In this scenario, only the second wrist joint (not shown) is assigned an articulation limit and the first wrist joint 803 is free to be articulated by control device 4.

FIG. 8C illustrates a surgical instrument 200 when a distance "d3" between the distal portion 801 of the surgical instrument 200 and a distal portion 850 of the access port 852 through which it is positioned is greater than both of the first threshold distance and the second threshold distance. In this scenario, both the first wrist joint 803 and the second wrist joint 805 are free to be controlled by control device 4 and are not assigned articulation limits.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A method of selectively controlling articulation limits of a surgical instrument, wherein a pre-set articulation limit of a tool of the surgical instrument is a function of a distance of a tool center point of the tool relative to a remote center of motion, the method comprising:
   detecting a proximal or a distal linear movement of the surgical instrument;
   after detecting the proximal or distal movement of the surgical instrument, calculating a distance between the tool center point of the tool of the surgical instrument, and the remote center of motion, wherein the tool center point represents a pivot point of the tool of the surgical instrument;
   when the detected linear movement is distal linear movement, assigning a binding articulation limit to the surgical instrument based on the calculated distance, wherein the binding articulation limit may not cross the pre-set articulation limit; and
   when the detected linear movement is proximal linear movement, assigning a non-binding articulation limit to the surgical instrument based on the calculated distance, wherein the non-binding articulation limit may cross the pre-set articulation limit.

2. The method of claim 1, further comprising:
   determining a current articulation angle of the surgical instrument when the detected linear movement is proximal linear movement; and
   determining when the current articulation angle of the surgical instrument is greater than the assigned non-binding articulation limit.

3. The method of claim 2, wherein, when the current articulation angle of the surgical instrument is greater than the assigned non-binding articulation limit, the current articulation angle of the surgical instrument is not impacted and the surgical instrument remains unbound by the non-binding articulation limit.

4. The method of claim 2, wherein, when the current articulation angle of the surgical instrument is not greater than the assigned non-binding articulation limit, the method further comprises:
   articulating the surgical instrument to a new articulation angle based on a received user command; and
   determining when the new articulation angle of the surgical instrument is less than the assigned non-binding articulation limit.

5. The method of claim 4, wherein, when the new articulation angle is determined to not be less than the assigned non-binding articulation limit, the new articulation angle of the surgical instrument is not impacted and the surgical instrument remains unbound by the non-binding articulation limit.

6. The method of claim 4, wherein, when the new articulation angle is determined to be less than the assigned non-binding articulation limit, the new articulation angle of the surgical instrument is not impacted and the method further comprises converting the non-binding articulation limit to the binding articulation limit.

7. The method of claim 1, wherein the binding articulation limit and the non-binding articulation limit are based on an articulation limit ramp including at least one of a linear, a quadratic, a power curve, or some other shape.

8. A robotic surgical system comprising:
   a surgical robotic arm including a surgical instrument disposed on a distal portion thereof; and
   a controller operably coupled to the surgical robotic arm, the controller configured to:

establish a software-based remote center of motion of the surgical instrument the surgical robot arm based on a location of a surgical portal in a patient through which the surgical instrument is inserted, wherein a pre-set articulation limit of a tool of the surgical instrument is a function of a distance of a tool center point relative to the remote center of motion;

detect a proximal or a distal linear movement of the surgical instrument;

after the proximal or the distal linear movement, calculate a distance between the tool center point of the tool of the surgical instrument and the remote center of motion, wherein the tool center point represents a pivot point of the tool of the surgical instrument;

when the detected linear movement is distal linear movement, assign a binding articulation limit to the surgical instrument based on the calculated distance, wherein the binding articulation limit may not cross the pre-set articulation limit; and when the detected linear movement is proximal linear movement, assign a non-binding articulation limit to the surgical instrument based on the calculated distance, wherein the non-binding articulation limit may cross the pre-set articulation limit.

9. The robotic surgical system of claim 8, wherein the controller is further configured to:
determine a current articulation angle of the surgical instrument when the detected linear movement is proximal linear movement; and
determine when the current articulation angle of the surgical instrument is greater than the assigned non-binding articulation limit.

10. The robotic surgical system of claim 9, wherein, when the current articulation angle of the surgical instrument is greater than the assigned non-binding articulation limit, the current articulation angle of the surgical instrument is not impacted and the surgical instrument remains unbound by the non-binding articulation limit.

11. The robotic surgical system of claim 9, wherein, when the current articulation angle of the surgical instrument is not greater than the assigned non-binding articulation limit, the controller is further configured to:
articulate the surgical instrument to a new articulation angle based on a received user command; and
determine when the new articulation angle of the surgical instrument is less than the assigned non-binding articulation limit.

12. The robotic surgical system of claim 11, wherein, when the new articulation angle is determined to not be less than the assigned non-binding articulation limit, the new articulation angle of the surgical instrument is not impacted and the surgical instrument remains unbound by the non-binding articulation limit.

13. The robotic surgical system of claim 11, wherein, when the new articulation angle is determined to be less than the assigned non-binding articulation limit, the new articulation angle of the surgical instrument is not impacted and the controller converts the non-binding articulation limit to the binding articulation limit.

14. A method of selectively controlling articulation limits of a tool of a surgical instrument, wherein a pre-set articulation limit of the tool of the surgical instrument is a function of a distance of a tool center point of the tool relative to a remote center of motion, wherein the tool center point represents a pivot point of the tool of the surgical instrument, the method comprising:
when the surgical instrument is moved in a proximal direction:
calculating a distance between the tool center point of the tool of the surgical instrument and the remote center of motion; and
assigning a non-binding articulation limit to the surgical instrument based on the calculated distance, wherein the non-binding articulation limit may cross the pre-set articulation limit; and
when the surgical instrument is moved in a distal direction:
calculating a distance between the tool center point of the tool of the surgical instrument and the remote center of motion; and
assigning a binding articulation limit to the surgical instrument based on the calculated distance, wherein the binding articulation limit may not cross the pre-set articulation limit.

15. The method of claim 14, further comprising:
determining a current articulation angle of the surgical instrument when the detected linear movement is proximal linear movement; and
determining when the current articulation angle of the surgical instrument is greater than the assigned non-binding articulation limit.

16. The method of claim 15, wherein, when the current articulation angle of the surgical instrument is greater than the assigned non-binding articulation limit, the current articulation angle of the surgical instrument is not impacted and the surgical instrument remains unbound by the non-binding articulation limit.

17. The method of claim 15, wherein, when the current articulation angle of the surgical instrument is not greater than the assigned non-binding articulation limit, the method further comprises:
articulating the surgical instrument to a new articulation angle based on a received user command; and
determining when the new articulation angle of the surgical instrument is less than the assigned non-binding articulation limit.

18. The method of claim 17, wherein, when the new articulation angle is determined to not be less than the assigned non-binding articulation limit, the new articulation angle of the surgical instrument is not impacted and the surgical instrument remains unbound by the non-binding articulation limit.

19. The method of claim 4, wherein, when the new articulation angle is determined to be less than the assigned non-binding articulation limit, the new articulation angle of the surgical instrument is not impacted and the method further comprises converting the non-binding articulation limit to the binding articulation limit.

* * * * *